United States Patent [19]
Horn et al.

[11] Patent Number: 5,486,904
[45] Date of Patent: Jan. 23, 1996

[54] METHOD FOR DETERMINING RESIN PARTICLES IN PAPER STOCKS

[75] Inventors: Dieter Horn, Heidelberg; Erik Lueddecke, Mutterstadt; Alfred Gierulski, Heidelberg-Ziegelhausen; Thomas Kroehl, Mainz; Primoz Lorencak, Ludwigshafen, all of Germany

[73] Assignee: BASF Aktiengesellschaft, Ludwigshafen, Germany

[21] Appl. No.: 70,414

[22] PCT Filed: Dec. 9, 1991

[86] PCT No.: PCT/EP91/02350
§ 371 Date: Jun. 7, 1993
§ 102(e) Date: Jun. 7, 1993

[87] PCT Pub. No.: WO92/11534
PCT Pub. Date: Jul. 9, 1992

[30] Foreign Application Priority Data

Dec. 18, 1990 [DE] Germany .......................... 40 40 463.3

[51] Int. Cl.$^6$ .......................... G01N 21/64; G01N 33/34; G01N 15/14
[52] U.S. Cl. .............................. 356/73; 356/318; 356/335; 356/441; 250/432 R; 250/459.1
[58] Field of Search ............................ 356/72, 335, 336, 356/317, 441, 442, 318, 417, 73; 250/432 R

[56] References Cited

U.S. PATENT DOCUMENTS

| | | | |
|---|---|---|---|
| 4,837,446 | 6/1989 | Renard et al. | 250/461.1 |
| 5,046,853 | 9/1991 | Hemel et al. | 356/440 |
| 5,216,483 | 6/1993 | Berthold et al. | 356/318 |

FOREIGN PATENT DOCUMENTS 1136032  11/1982  Canada .

OTHER PUBLICATIONS

Norman, "Flow Cytometry", Nov./Dec. 1980, vol. 7, No. 6, Medical Physics pp. 609–615.

Primary Examiner—Robert P. Limanek
Assistant Examiner—David B. Hardy
Attorney, Agent, or Firm—Keil & Weinkauf

[57] ABSTRACT

The free resin particles which present problems in papermaking are determined according to number and size in order to bind them to the wood fibers by adding assistants and hence render them harmless. For this purpose, a paper stock suspension is prepared and the resin particles are separated from said suspension and then marked with a fluorescent dye and isolated. The light signals emitted by the individual resin particles after excitation are detected for determination of number and size.

5 Claims, 3 Drawing Sheets

METHOD FOR DETERMINING RESIN PARTICLES IN PAPER STOCKS

BACKGROUND OF THE INVENTION

1. Field of Invention

The present invention relates to a method for determining the number and size of resin particles freely distributed in paper stock.

2. Description of the Prior Art

In papermaking by a procedure at neutral pH, the natural resin particles present in the paper stock give rise to problems. In particular, the free resin particles, ie. those which are not bound to the wood fibers, are deposited in the paper machines and hence lead to considerable operating problems, for example tears in the paper, and consequently to expensive downtimes. Assistants which bind the resin particles to the wood fibers and thus ensure that the resin is discharged with the paper from the paper machine are therefore added to the paper stock. The efficiency of such assistants has been tested to date by expensive and not very reliable tests on the paper machines themselves. Furthermore, the literature describes methods which permit determination of the harmful amount of resin in the laboratory. However, the detection of free resin particles and testing of the efficiency of the assistants used is made very difficult on the laboratory scale by virtue of the fact that the unbound resin is present only in very small amounts in the paper stock (about 1 g of free resin to 1 tonne of paper stock). The known, conventional methods of determination of harmful resin, such as the extraction of the paper stock with organic solvents, for example with dichloromethane (Weigl et al., Das Papier 40 (1986), V52), the deposition of the resin on surfaces, for example according to Gustafson (Gustafson C. et al., Paperi ja Puu 34 (1952), 121–127), the flotation method according to Störle and Teves (Störle and Teves, Das Papier 10 (1956), 264–170) and the microscopic counting method (Allen, L. H., Pulp & Paper, Canada, 76 (1975), 70) thus give unsatisfactory and controversial results.

SUMMARY OF THE INVENTION

It is an object of the present invention to provide a method for determining the number and the size of resin particles freely distributed in paper stock, which can be carried out reliably without great expense, even at a very low concentration of dispersed resin in the paper stock.

We have found that this object is achieved by the method according to the invention, wherein a paper stock suspension is first prepared and the resin particles are separated from said suspension by filtration, after which the resin particles are marked with a fluorescent dye, isolated and then excited to produce light emission, the light signals of the individual resin particles are detected and the detection signals are evaluated for counting and size determination of the resin particles.

The method is described in detail below for an example, with reference to the drawing.

DESCRIPTION OF THE PREFERRED EMBODIMENTS

Figure 1:
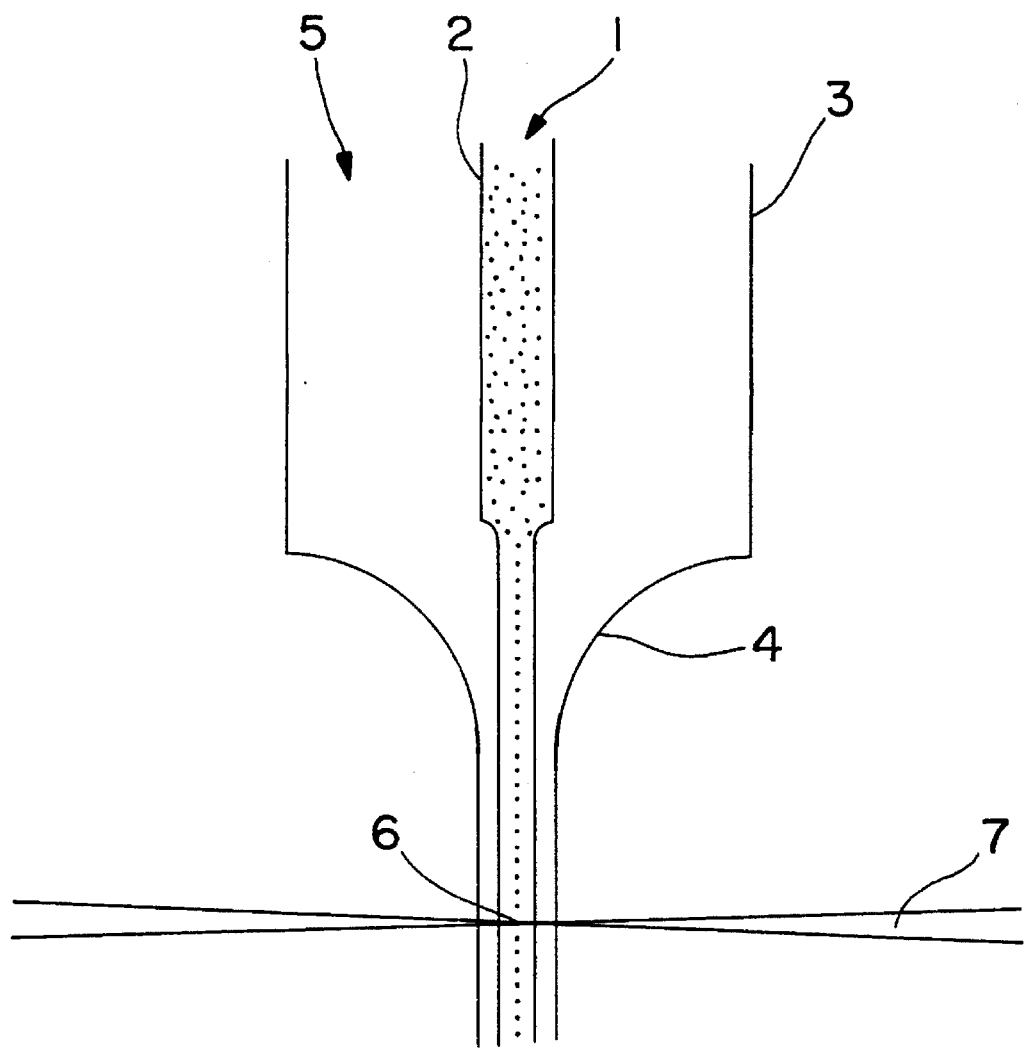
FIG. 1 shows a schematic longitudinal section of a measuring cell for isolating the resin particles.

After preparing a suspension from the paper stock to be investigated and water, the suspension is filtered to separate the resin particles from the paper stock.

This is done using a dynamic drainage jar, a Plexiglas container with an integral paper sieve of 80 µm mesh size, by first diluting the paper stock to be investigated to a solids content of about 0.4% (value used in practice) and filtering the stirred stock through the sieve. The assistant for binding the resin particles to the wood fibers is added to the dilute paper stock suspension before filtration, in a concentration of from 0 to 0.5%, based on the fiber solids content. The filtrate obtained, which contains resin particles and fibers smaller than 80 µm, is further diluted (1:10), and a dye solution, preferably the fluorescent dye Fluorol® from BASF AG (N-(n-butyl)-4-(n-butylamino)naphthalimide) in solution in a concentration of 40 mg/l of ethanol, is added in a ratio of 1:25. Only the resin particles are dyed, not the wood fibers. After a dyeing time of about 2 minutes, the actual measurement can be started.

Determination of the number and size of resin particles can be carried out on isolated, flowing particles using both a coherent, elastic, angle-dependent light scattering process and the incoherent, angle-independent scattering phenomenon of fluorescence. In both cases, the particles are illuminated individually by a laser beam.

Isolation of the resin particles is effected by the principle of hydrodynamic focusing, where the particle suspension is introduced into an envelope stream of flowing water in an envelope stream cell and is diluted by the flow rate of the envelope stream, which is substantially higher relative to the sample stream, and the particles are hydrodynamically focused in the center of the common water jet and then passed through a focused laser beam.

To excite the fluorescent dyes, which generally absorb in the blue wavelength range, the laser line which best fits the absorption maximum is used. The generally yellow fluorescent light (about 550 nm) is fed to a detector, for example a photomultiplier, via an edge filter and a lens, at an angle of observation of 90°. The edge filter shields the photomultiplier from the scattered blue laser light used for excitation.

The individual photomultiplier signals are amplified and fed to a multichannel analyzer. There, the signals are sorted according to their intensity, counted, and represented as a pulse height diagram. The amplified signals are simultaneously fed to an oscilloscope in order to adjust the apparatus and check the measurement. The counting time per measurement is 100 s. The multi-channel analyzer is integrated in a personal computer, in which the recorded data is stored and evaluated.

The fluorescence intensity is proportional to the volume of the particles, since it may be assumed that the number of fluorescent molecules per unit volume is constant for each particle. The pulse height thus indicates the size of the counted resin particles. The apparatus is calibrated using fluorescence-marked calibration latices of known size.

With the aid of the method according to the invention, it is possible to record pulse height distributions of paper stock filtrates with and without the addition of assistants and to determine the particular resin particle count as the sum of channel contents. The percentage decrease in the resin particle count after the addition of the assistant is used as a measure of the efficiency of the assistants employed.

The structure of the measuring cell for isolating and detecting the resin particles is shown schematically in FIG.

1. The paper stock filtrate 1 is passed through a capillary 2 (diameter=100 μm) into an envelope stream cell 3, at the end of which is a nozzle 4 having a diameter of 200 μm. The flow rate of the envelope stream 5, which is higher relative to the sample stream 1 (ratio 100:1), results in dilution of the particle suspension and leads to hydrodynamic focusing of the resin particles in the center of the common liquid jet. The resin particles are thus conveyed individually in a free-falling jet through measuring point 6, which coincides with the focus of the laser beam 7.

Figure 2:
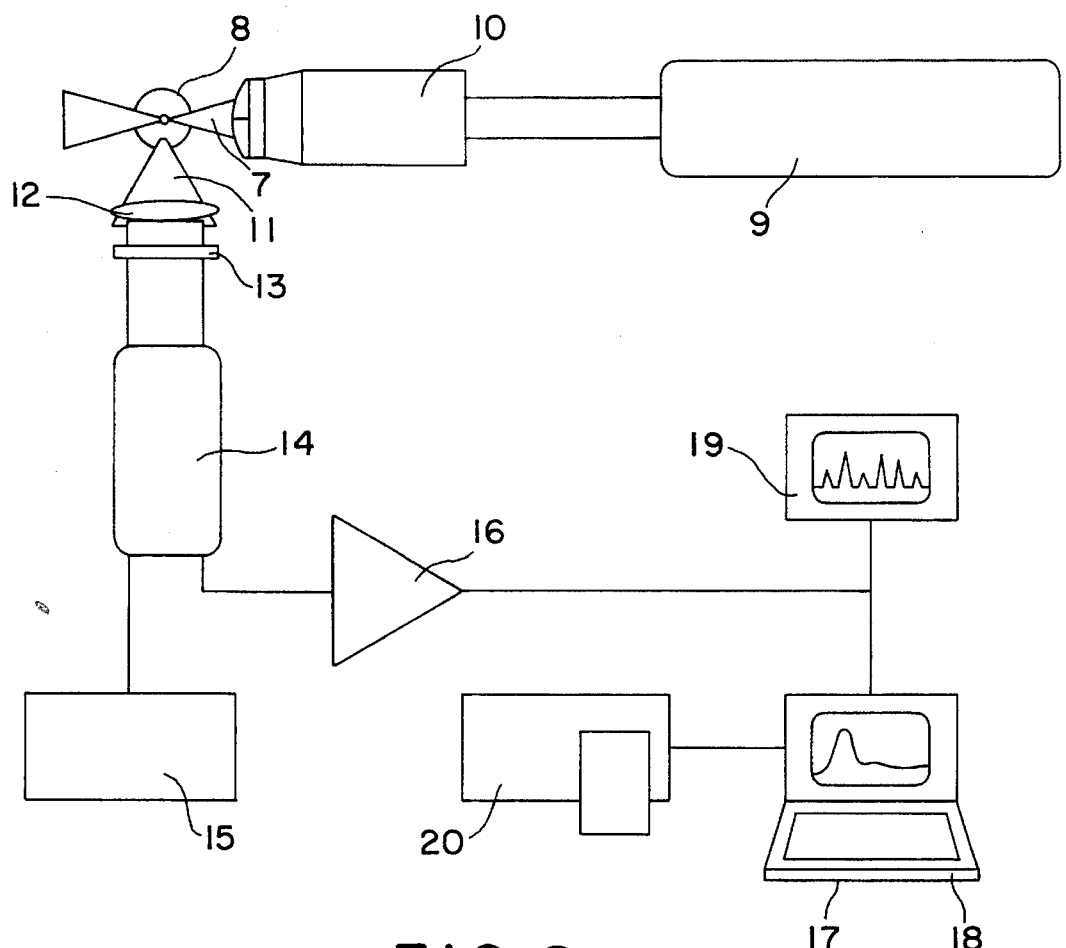
FIG. 2 shows a measuring arrangement for carrying out the method and FIG. 3 is a graph showing the dependence of the number of resin particles on the assistant concentration.

The complete measuring arrangement in which the measuring cell of FIG. 1 is integrated is shown in FIG. 2. The resin particles isolated by hydrodynamic focusing pass, in measuring cell 8, through the focal point of the laser beam 7, which is obtained by focusing a laser 9 on the center of the measuring cell by means of a lens 10. The fluorescent light 11 emitted by the marked resin particles is fed at right angles to the exciting beam and at right angles to the sample stream, via a lens 12 and an edge filter 13, to a photomultiplier 14, which is supplied with high voltage by the voltage unit 15. The electrical signals from the photomultiplier are logarithmically amplified in an amplifier 16 and then fed to a multichannel analyzer 17, which is integrated in a personal computer 18. For adjusting the apparatus and checking the measurement, the signals are simultaneously represented on an oscillograph 19. The recorded pulse height diagrams and the evaluated measurements can be output on a plotter/printer 20.

The apparatus used according to the invention can be used in practice for process control in papermaking, with regard to harmful resin in the paper stock. With the information about the amount of harmful resin, which is obtained by the method according to the invention, it is possible to control the feed of assistants to the headbox.

Figure 3:
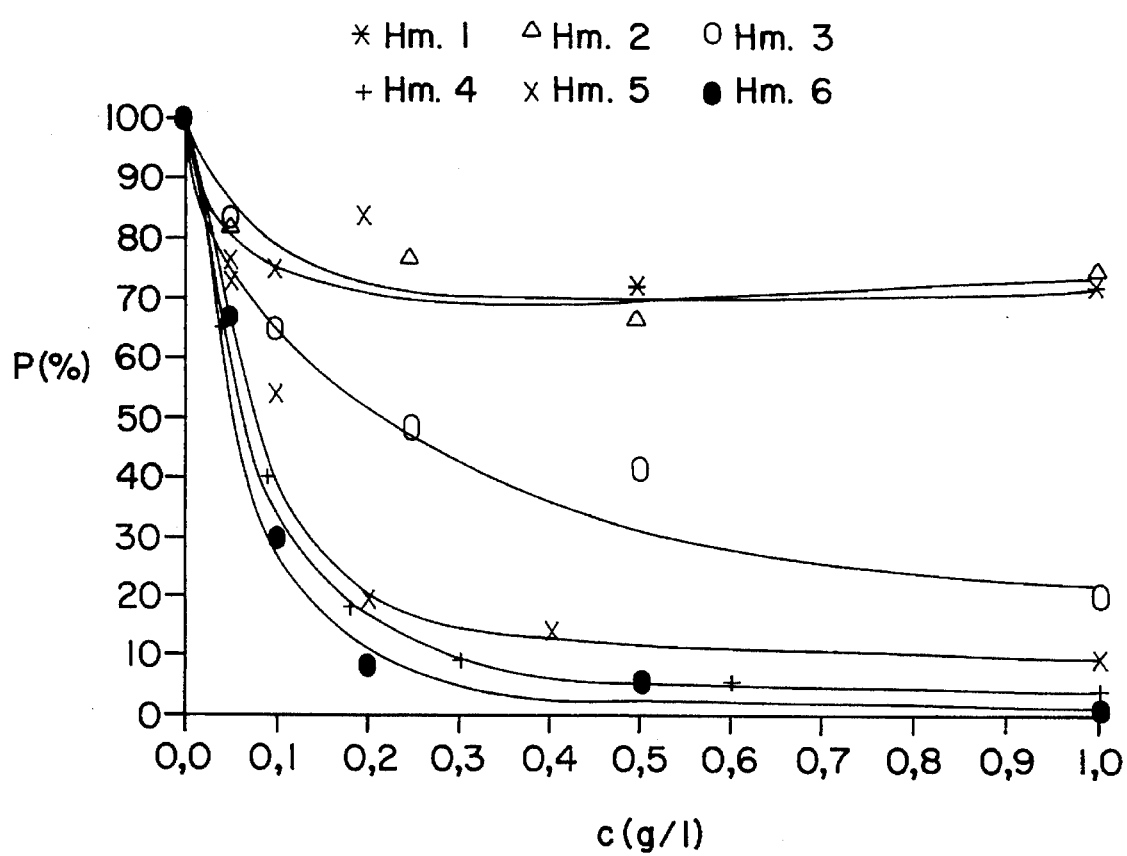

FIG. 3 shows a graph of the results of the measurements for different assistant concentrations (Hm1-Hm6). The percentage P [%] of resin particles still present in the filtrate is plotted as a function of the assistant concentration C [g/l]. The measuring points each represent the ratio of the area under the distribution curve with assistant to that under the curve without assistant. The Figure shows not only the decrease in the resin particle count for each assistant but also the different efficiencies of the assistants.

The fluorescent dye Fluorol 555 (N-(n-butyl)-4-(n-butylamino)-naphthalimide) was used for dyeing the dispersed resin particles. The absorption maximum of the dye is at 440 nm. The 442 nm line of a He-Cd laser is therefore preferably used for excitation. When other fluorescent dyes are used, the laser and the edge filter must be correspondingly adjusted.

We claim:

1. A method for analyzing resin particles freely distributed in paper stock to determine the number and size of the particles which comprises: forming a suspension of the paper stock in water; separating the resin particles from the suspension by filtration; marking the separated particles with a fluorescent dye; isolating the marked particles; exciting the particles to produce light emission signals, and detecting the light emission signals and evaluating the signals to count the marked particles and to determine the size of the marked particles.

2. A method as defined in claim 1, wherein the resin particles are isolated by hydrodynamic focusing in an envelope stream cell.

3. A method as defined in claim 1, wherein excitation of the resin particles for light emission is caused by passing the particles through a laser beam.

4. A method as defined in claim 1, wherein the fluorescent dye used is N-(n-butyl)-4-(n-butylamino)-naphthalimide.

5. A method as defined in claim 1, wherein a photomultiplier is used to detect the light signals of the resin particles, and wherein the signals from the photomultiplier are evaluated in a multichannel analyzer.

* * * * *